(12) United States Patent
Son et al.

(10) Patent No.: US 10,535,862 B2
(45) Date of Patent: Jan. 14, 2020

(54) SYSTEM FOR MANUFACTURING ELECTRODE FOR SECONDARY BATTERY HAVING SCRATCH TESTER

(71) Applicant: LG CHEM, LTD., Seoul (KR)

(72) Inventors: Jin-Young Son, Daejeon (KR);
Jung-Min Yang, Daejeon (KR);
Taek-Soo Lee, Daejeon (KR);
Chan-Soo Jun, Daejeon (KR);
Hyung-Suk Cho, Daejeon (KR);
Sang-Hoon Choy, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/094,181

(22) PCT Filed: Nov. 30, 2017

(86) PCT No.: PCT/KR2017/013961
§ 371 (c)(1),
(2) Date: Oct. 16, 2018

(87) PCT Pub. No.: WO2018/128277
PCT Pub. Date: Jul. 12, 2018

(65) Prior Publication Data
US 2019/0140253 A1 May 9, 2019

(30) Foreign Application Priority Data

Jan. 3, 2017 (KR) .................. 10-2017-0000871

(51) Int. Cl.
*H01M 10/14* (2006.01)
*H01M 4/04* (2006.01)
(Continued)

(52) U.S. Cl.
CPC ............ *H01M 4/0404* (2013.01); *G01N 3/46* (2013.01); *H01M 4/0471* (2013.01);
(Continued)

(58) Field of Classification Search
CPC .. H01M 4/0404; H01M 4/0471; H01M 4/139; H01M 10/4285; H01M 2004/021; G01N 3/46
See application file for complete search history.

(56) References Cited

U.S. PATENT DOCUMENTS

2006/0169596 A1* 8/2006 Goto ...................... C23C 26/00
205/640
2012/0295037 A1* 11/2012 Hagiwara ........... H01M 4/0404
427/542
(Continued)

FOREIGN PATENT DOCUMENTS

DE  102012224233 A1  6/2014
JP  3-264841 A  11/1991
(Continued)

OTHER PUBLICATIONS

International Search Report for PCT/KR2017/013961 (PCT/ISA/210) dated Mar. 30, 2018.

*Primary Examiner* — Raymond Alejandro
(74) *Attorney, Agent, or Firm* — Birch, Stewart, Kolasch & Birch, LLP (57) ABSTRACT

Disclosed is a system for manufacturing an electrode for a secondary battery, which includes an active material drying unit configured to dry an active material coated on an electrode current collector, and a tester unit configured to measure a dried state of the active material by performing a scratch test to the dried active material.

9 Claims, 6 Drawing Sheets

(51) Int. Cl.
  *G01N 3/46* (2006.01)
  *H01M 10/42* (2006.01)
  *H01M 4/139* (2010.01)
  *H01M 4/02* (2006.01)

(52) U.S. Cl.
  CPC ....... *H01M 4/139* (2013.01); *H01M 10/4285* (2013.01); *H01M 2004/021* (2013.01)

(56) References Cited

U.S. PATENT DOCUMENTS

| | | | |
|---|---|---|---|
| 2013/0164618 A1 | 6/2013 | Konishi | |
| 2013/0309569 A1* | 11/2013 | Tsujiko | H01M 4/70 |
| | | | 429/211 |
| 2014/0113063 A1 | 4/2014 | Nakano | |
| 2015/0086866 A1 | 3/2015 | Park et al. | |
| 2015/0255780 A1 | 9/2015 | Tsuchiya | |
| 2016/0351290 A1* | 12/2016 | Kim | H01B 1/22 |

FOREIGN PATENT DOCUMENTS

| | | |
|---|---|---|
| JP | 11-176422 A | 7/1999 |
| JP | 2001-176502 A | 6/2001 |
| JP | 2015-125900 A | 7/2015 |
| JP | 6011478 B2 | 10/2016 |
| KR | 10-2006-0027260 A | 3/2006 |
| KR | 10-2007-0092385 A | 9/2007 |
| KR | 10-2012-0057437 A | 6/2012 |
| KR | 10-2013-0076758 A | 7/2013 |
| KR | 10-1475429 B1 | 12/2014 |
| KR | 10-2015-0058351 A | 5/2015 |

* cited by examiner

SYSTEM FOR MANUFACTURING ELECTRODE FOR SECONDARY BATTERY HAVING SCRATCH TESTER

TECHNICAL FIELD

The present disclosure relates to a system for manufacturing an electrode for a secondary battery having a scratch tester, and more particularly, to a system for manufacturing an electrode for a secondary battery having a scratch tester, which is used to check a dried state of an electrode active material coated on an electrode current collector.

The present application claims priority to Korean Patent Application No. 10-2017-0000871 filed on Jan. 3, 2017 in the Republic of Korea, the disclosures of which are incorporated herein by reference.

BACKGROUND ART

An electrode used for a secondary battery is manufactured by coating an electrode current collector with an electrode active material and drying the electrode in a drying furnace. The degree of drying of the coated electrode active material has a close relation with the occurrence of a defect during a process of drying the corresponding electrode, which is performed later.

That is, if the drying is not sufficiently performed, a defect may occur due to contamination and/or separation of the electrode active material while the electrode is being carried in a roll-to-roll manner. On the contrary, if the drying is performed excessively, there is a high possibility of a brittle fracture phenomenon, namely a phenomenon that the electrode is not flexibly deformed but broken due to its brittle feature while being manufactured.

As described above, the dried state of the electrode active material coated on the electrode current collector is an important factor to determine whether a defect occurs in subsequent processes. However, in order to figure out the dried state of the electrode under coating, it is inevitable to stop the operation of the manufacturing equipment at least partially.

In other words, in the existing technique, in order to figure out the dried state of the electrode active material during the electrode manufacturing process, it is necessary that the operation of the equipment is stopped at least partially and then an operator performs diagnosis through visual and touching, thereby deteriorating the overall productivity for the electrode. In addition, since it is difficult to apply a consistent standard in relation to the degree of drying, the quality of the product may not be kept constantly.

DISCLOSURE

Technical Problem

The present disclosure is designed to solve the problems of the related art, and therefore the present disclosure is directed to figuring out a dried state of an electrode active material without stopping the operation of the electrode manufacturing equipment, and also suitably changing conditions applied to a drying furnace according to the dried state of the electrode active material to improve the product quality and the productivity.

However, the technical problem to be solved by the present disclosure is not limited to the above, and other objects not mentioned herein will be clearly understood by those skilled in the art from the following present disclosure.

Technical Solution

In one aspect of the present disclosure, there is provided a system for manufacturing an electrode for a secondary battery, comprising: an active material drying unit configured to dry an active material coated on an electrode current collector; and a tester unit configured to measure a dried state of the active material by performing a scratch test to the dried active material.

The tester unit may measure a force applied to the tester unit when a scratch is generated at the electrode active material.

The system for manufacturing an electrode for a secondary battery may further comprise a control unit configured to control a drying temperature of the drying unit according to a change of the force measured by the tester unit.

The system for manufacturing an electrode for a secondary battery may further comprise a carrying unit configured to carrying the electrode current collector and the electrode.

The system for manufacturing an electrode for a secondary battery may further comprise a coating unit configured to coat an electrode active material on the electrode current collector.

The tester unit may include a scratch tester located on an electrode active material completely dried by the drying unit to generate a scratch on the electrode active material as the electrode moves.

The tester unit may further include a rotary shaft connected to the scratch tester and installed so that the scratch tester is rotatable thereon.

The tester unit may further include a torque sensor configured to measure a torque applied to the rotary shaft when the scratch is generated.

The system for manufacturing an electrode for a secondary battery may further comprise a display unit configured to display the dried state of the active material, measured by the tester unit.

Advantageous Effects

According to an embodiment of the present disclosure, it is possible to figure out a dried state of the electrode active material without stopping the operation of the electrode manufacturing equipment while an electrode is being manufactured, thereby improving the productivity.

In addition, according to another embodiment of the present disclosure, it is possible to improve the quality of the product by suitably changing conditions applied to a drying furnace according to the dried state of the electrode active material.

DESCRIPTION OF DRAWINGS

The accompanying drawings illustrate a preferred embodiment of the present disclosure and together with the foregoing disclosure, serve to provide further understanding of the technical features of the present disclosure, and thus, the present disclosure is not construed as being limited to the drawing.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

Referring to FIGS. 1 to 4, a system for manufacturing an electrode for a secondary battery according to an embodiment of the present disclosure will be described in detail.

Figure 1:
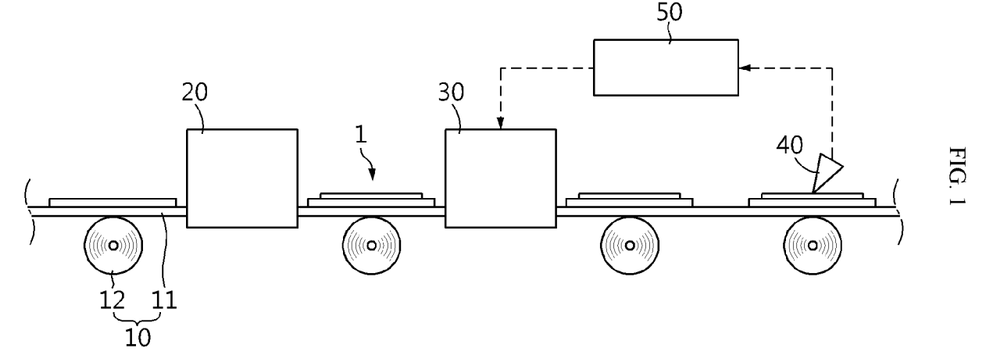
FIG. 1 is a diagram showing a system for manufacturing an electrode for a secondary battery according to an embodiment of the present disclosure.
Figure 2:
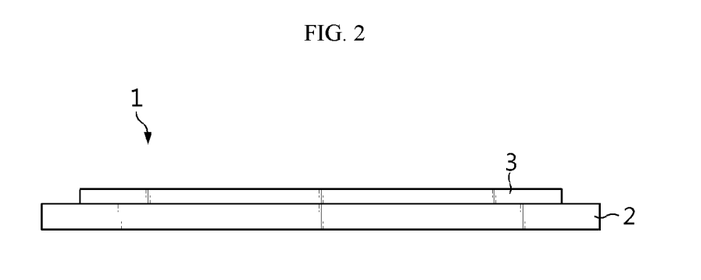
FIG. 2 is a diagram showing an example of the electrode for a secondary battery of FIG. 1.
Figure 3:
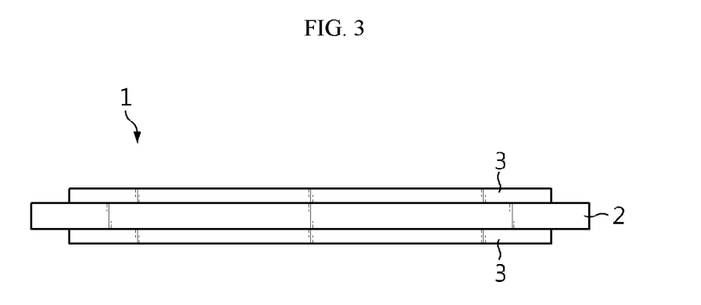
FIG. 3 is a diagram showing another example of the electrode for a secondary battery of FIG. 1.
Figure 4:
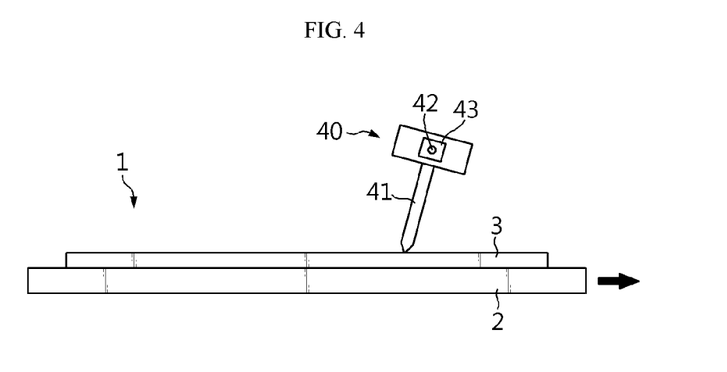
FIG. 4 is a diagram showing an example of a scratch tester employed in the present disclosure.

FIG. 1 is a diagram showing a system for manufacturing an electrode for a secondary battery according to an embodiment of the present disclosure, FIG. 2 is a diagram showing an example of the electrode for a secondary battery of FIG. 1, FIG. 3 is a diagram showing another example of the electrode for a secondary battery of FIG. 1, and FIG. 4 is a diagram showing an example of a scratch tester employed in the present disclosure.

First, referring to FIG. 1, a system for manufacturing an electrode for a secondary battery according to an embodiment of the present disclosure includes a carrying unit 10, an active material coating unit 20, an active material drying unit 30 and a tester unit 40, and may further include a control unit 50.

The carrying unit 10 carries an electrode 1 for a secondary battery and an electrode current collector 2 applied thereto. For example, the carrying unit 10 may include a carrying belt 11 and a plurality of carrying rollers 12 for moving the carrying belt 11 in a horizontal direction so that an object placed on the carrying belt 11 is moved.

The active material coating unit 20 coats an electrode active material 3 on the electrode current collector 2 carried by the carrying unit 10. The electrode active material 3 may be coated on only one surface of the electrode current collector 2 (see FIG. 2) or may be coated on both surfaces of the electrode current collector 2 (see FIG. 3).

The active material drying unit 30 dries the electrode active material 3 coated on the electrode current collector 2 by the active material coating unit 20 so that the electrode active material 3 is not contaminated or separated in following processes using the electrode 1 for a secondary battery.

The active material drying unit 30 is dried at an appropriate temperature with an appropriate time condition according to the type of the electrode active material 3 used. If the electrode active material 3 is insufficiently dried, the electrode active material 3 may be contaminated or separated. On the contrary, if the electrode active material 3 is excessively dried, the electrode active material 3 may become brittle and cause brittle fracture when the electrode 1 is wound.

The tester unit 40 inspects the dried state of the electrode active material 3 completely dried while passing through the active material drying unit 30.

If the tester unit 40 measures the dried state, a scratch is generated at the electrode active material 3, and it is performed by measuring a force applied to the tester unit 40 when the scratch is generated.

The detailed configuration of the tester unit 40 is not specially limited as long as it is capable of generating a scratch at the electrode active material 3 and measuring the force applied to the tester unit 40 when a scratch is generated.

Referring to FIG. 4, an example of the tester unit 40 is depicted.

Referring to FIG. 4, the tester unit 40 employed in the present disclosure may include a scratch tester 41 located on the electrode 1 carried in an arrowed direction and having a sharp end to cause a scratch at the surface of the electrode active material 3. In addition, the tester unit 40 may include a rotary shaft 42 connected to the scratch tester 41 so that the scratch tester may be rotated around one end thereof, and a torque sensor 43 for measuring a force applied to the rotary shaft 42.

However, the structure of the tester unit 40 shown in FIG. 4 is merely illustrative of an exemplary structure of the tester unit 40, and the structure of the tester unit 40 employed in the present disclosure is not limited thereto. That is, the tester unit 40 employed in the present disclosure is not specially limited as long as it has a structure capable of measuring the force applied to the tester unit 40 in the scratch test.

Next, referring to FIGS. 5 to 10, a process of determining a dried state by the tester unit 40 will be described.

Figure 5:
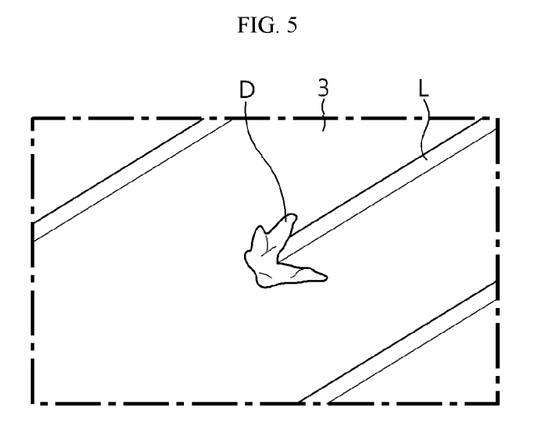
FIG. 5 is a diagram showing a scratch shown on the surface of the electrode active material when the electrode active material is insufficiently dried.
Figure 6:
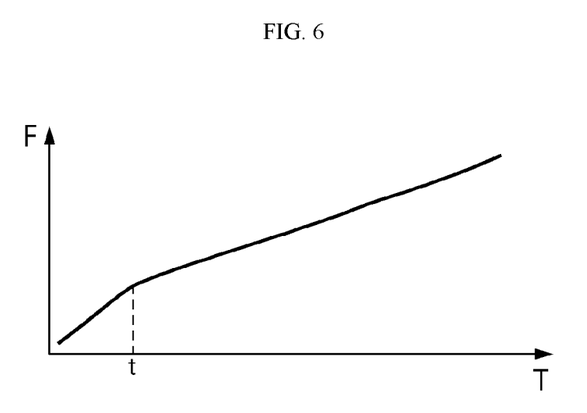
FIG. 6 is a graph showing a change in the magnitude of force, sensed by a scratch tester according to time, when a scratch is generated as shown in FIG. 5.
Figure 7:
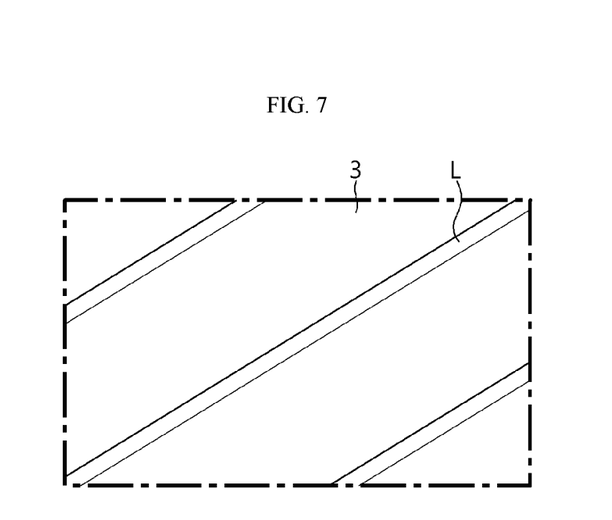
FIG. 7 is a diagram showing a scratch shown on the surface of the electrode active material when the electrode active material is appropriately dried.
Figure 8:
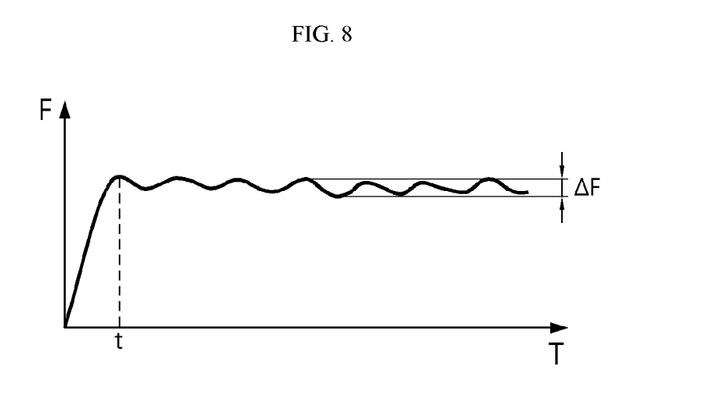
FIG. 8 is a graph showing a change in the magnitude of force, sensed by the scratch tester according to time, when a scratch is generated as shown in FIG. 7.
Figure 9:
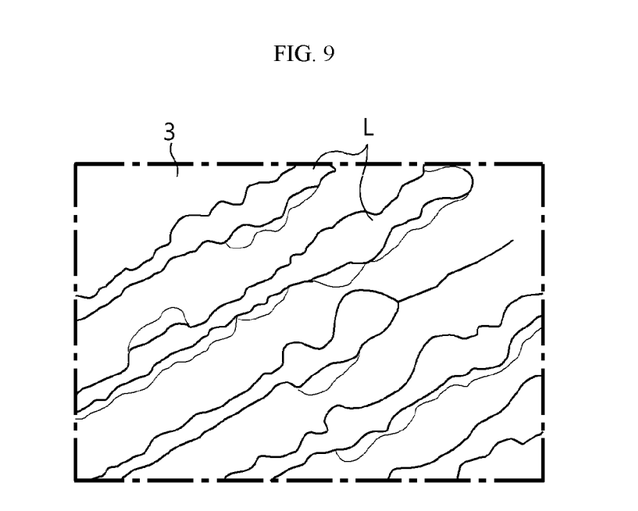
FIG. 9 is a diagram showing a scratch shown on the surface of the electrode active material when the electrode active material is excessively dried.
Figure 10:
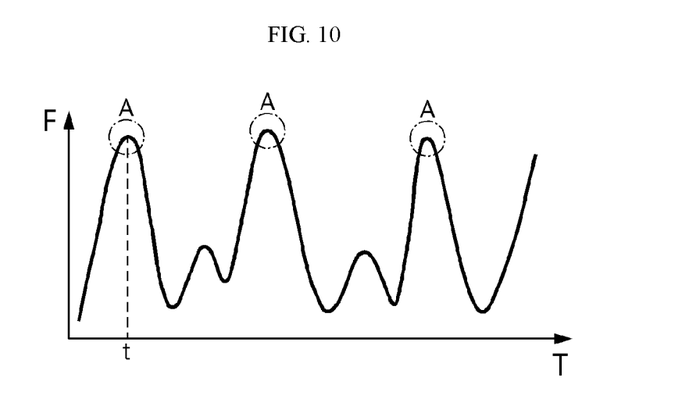
FIG. 10 is a graph showing a change in the magnitude of force, sensed by the scratch tester according to time, when a scratch is generated as shown in FIG. 9.

FIG. 5 is a diagram showing a scratch shown on the surface of the electrode active material when the electrode active material is insufficiently dried, and FIG. 6 is a graph showing a change in the magnitude of force, sensed by a scratch tester according to time, when a scratch is generated as shown in FIG. 5. In addition, FIG. 7 is a diagram showing a scratch shown on the surface of the electrode active material when the electrode active material is appropriately dried, and FIG. 8 is a graph showing a change in the magnitude of force, sensed by the scratch tester according to time, when a scratch is generated as shown in FIG. 7. In addition, FIG. 9 is a diagram showing a scratch shown on the surface of the electrode active material when the electrode active material is excessively dried, and FIG. 10 is a graph showing a change in the magnitude of force, sensed by the scratch tester according to time, when a scratch is generated as shown in FIG. 9.

First, referring to FIG. 5, if the electrode active material 3 is not sufficiently dried, a scratch is generated at the electrode active material 3 by the tester unit 40, and thus it may be found that an active material deposit accumulates. If the active material deposit D accumulates as described above as a scratch line L is formed in the scratch test, the magnitude of force applied to the tester unit 40 also tends to increase as the scratch test progresses.

This tendency may be found in the graph of FIG. 6. Seeing the graph of FIG. 6, it may be found that the slope indicating a change rate of the force with respect to time appears somewhat larger at an early stage of the scratch test (until a time t elapses), but after a certain period of time lapses, the slope is slightly decreased compared to the initial stage. This tendency is because the resistance applied the tester unit 40 increases as the amount of deposit accumulated by the scratch increases according to the test time.

Next, referring to FIG. 7, if the electrode active material 3 is dried appropriately, it may be found that there is no trace of deposit accumulation or partial separation of the active material as the scratch line L is formed.

This tendency may be found in the graph of FIG. 8. Namely, seeing the graph of FIG. 8, it may be found that except for the initial stage of the scratch test, the change of the force according to the test time of the test is substantially constant, and thus the maximum change ($\Delta F$) of the force is not large.

The range of $\Delta F$ for evaluating that the electrode active material 3 is dried appropriately may vary depending on the type of electrode active material. That is, an operator selects an allowable maximum value of the $\Delta F$ value according to the type of the electrode active material and determines that drying is performed normally only when a $\Delta F$ value obtained by the test is derived to be smaller than the allowable maximum value.

Next, referring to FIG. 9, if the electrode active material 3 is excessively dried, it may be found that a brittle fracture occurs partially at the electrode active material 3 as the scratch line L is formed. Due to the excessively dried electrode active material 3, the force for generating a scratch becomes greater and greater. Also, if a force over a certain level is applied, the electrode active material 3 is partially fractured, and then the magnitude of force required to form the scratch is reduced. This process is repeated.

This tendency may be found in the graph of FIG. 10. Namely, seeing the graph of FIG. 10, it may be found that the magnitude of the force gradually increases as the test progresses from the initial stage of the scratch test, and at a certain level (a point A), the electrode active material 3 is fractured and the magnitude of the force is greatly decreased. And then, the magnitude of the force is increased again as a scratch is generated, and the electrode active material is fractures and the magnitude of the force is greatly decreased, repeatedly.

As described above, if the change of the force applied to the tester unit 40 is very large as the scratch test progresses, it may be determined that the electrode active material 3 is excessively dried.

Meanwhile, referring to FIG. 1 again, the system for manufacturing an electrode for a secondary battery according to an embodiment of the present disclosure may further include a control unit 50. The control unit 50 may raise or lower the drying temperature by controlling the drying unit 30 according to the change of the force measured by the tester unit 40.

In other words, the control unit 50 may receive the information about the force measured by the tester unit 40, analyze the change of the force according to the time, determine that the drying is insufficient when the analysis result indicates that the force continuously increases according to time, and output a control signal for raising the drying temperature.

In addition, when the force increases according to time and then repeats increasing and decreasing after a certain time elapses, the control unit 50 may determine that the drying is excessive if the maximum increase/decrease of the force is greater than a preset reference value, and then output a control signal for lowering the drying temperature. Also, if the temperature does not exceed the reference value, the control unit 50 may not send a separate control signal so that the current drying temperature is maintained.

Next, a system for manufacturing an electrode for a secondary battery according to another embodiment of the present disclosure will be described with reference to FIG. 11.

Figure 11:
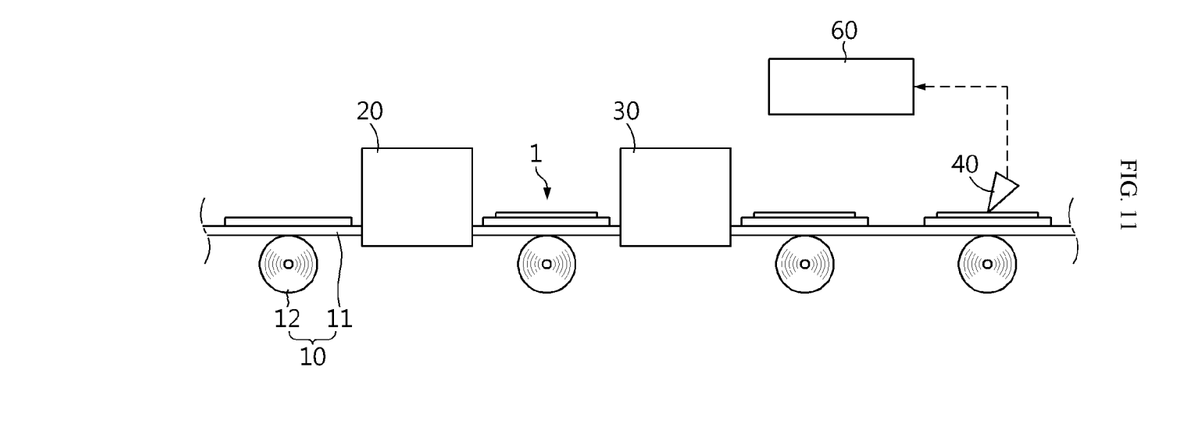
FIG. 11 is a diagram showing a system for manufacturing an electrode for a secondary battery according to another embodiment of the present disclosure.

FIG. 11 is a diagram showing a system for manufacturing an electrode for a secondary battery according to another embodiment of the present disclosure.

Referring to FIG. 11, the system for manufacturing an electrode for a secondary battery according to another embodiment of the present disclosure further includes a display unit 60, compared to the system for manufacturing an electrode as shown in FIG. 1.

The display unit 60 displays the dried state of the active material measured by the tester unit 40 so that a user may check the dried state of the active material and thereby control the drying temperature of the active material drying unit 30.

Meanwhile, though not shown in the figures, the display unit 60 may also be applied together with the control unit 50. If the display unit 60 and the control unit 50 are applied together in this way, the control unit 50 may calculate the amount of temperature to be adjusted by an operator according to the measurement result of the tester unit 40 and display the calculation result through the display unit 60.

As described above, if the system for manufacturing an electrode for a secondary battery according to the present disclosure is used, it is possible to figure out the dried state of the electrode active material without stopping the operation of the equipment during the electrode manufacturing process, and it is also possible to appropriately change the conditions applied to a drying furnace according to the dried state of the electrode active material, thereby improving the product quality and productivity.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A system for manufacturing an electrode for a secondary battery, comprising:
   an active material drying unit configured to dry an active material coated on an electrode current collector; and
   a tester unit configured to measure a dried state of the active material by performing a scratch test to the dried active material.

2. The system for manufacturing an electrode for a secondary battery according to claim 1,
wherein the tester unit measures a force applied to the tester unit when a scratch is generated at the electrode active material.

3. The system for manufacturing an electrode for a secondary battery according to claim 2, further comprising:
a control unit configured to control a drying temperature of the drying unit according to a change of the force measured by the tester unit.

4. The system for manufacturing an electrode for a secondary battery according to claim 1, further comprising:
a carrying unit configured to carrying the electrode current collector and the electrode.

5. The system for manufacturing an electrode for a secondary battery according to claim 1, further comprising:
a coating unit configured to coat an electrode active material on the electrode current collector.

6. The system for manufacturing an electrode for a secondary battery according to claim 1,
wherein the tester unit includes a scratch tester located on an electrode active material completely dried by the drying unit to generate a scratch on the electrode active material as the electrode moves.

7. The system for manufacturing an electrode for a secondary battery according to claim 6,
wherein the tester unit further includes a rotary shaft connected to the scratch tester and installed so that the scratch tester is rotatable thereon.

8. The system for manufacturing an electrode for a secondary battery according to claim 7,
wherein the tester unit further includes a torque sensor configured to measure a torque applied to the rotary shaft when the scratch is generated.

9. The system for manufacturing an electrode for a secondary battery according to claim 1, further comprising:
a display unit configured to display the dried state of the active material, measured by the tester unit.

* * * * *